United States Patent
Tanavade et al.

(10) Patent No.: US 11,395,792 B2
(45) Date of Patent: Jul. 26, 2022

(54) ORAL CARE COMPOSITION

(71) Applicant: RHODIA OPERATIONS, Aubervilliers (FR)

(72) Inventors: Juie Tanavade, Hillsborough, NJ (US); Marivi Ortiz-Suarez, Burlington, NJ (US); Alexandre Graet, New York, NY (US); Laurianne Timbart, Bensalem, PA (US)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 16/892,413

(22) Filed: Jun. 4, 2020

(65) Prior Publication Data

US 2020/0390672 A1 Dec. 17, 2020

Related U.S. Application Data

(60) Provisional application No. 62/857,425, filed on Jun. 5, 2019.

(51) Int. Cl.
| | |
|---|---|
| *A61K 8/43* | (2006.01) |
| *A61K 8/41* | (2006.01) |
| *A61Q 11/00* | (2006.01) |
| *A61K 8/81* | (2006.01) |
| *A61K 8/24* | (2006.01) |

(52) U.S. Cl.
CPC ............... *A61K 8/43* (2013.01); *A61K 8/24* (2013.01); *A61K 8/416* (2013.01); *A61K 8/8147* (2013.01); *A61K 8/8164* (2013.01); *A61Q 11/00* (2013.01)

(58) Field of Classification Search
CPC ................................ A61K 7/16; A61Q 11/00
USPC ............................................................. 424/49
See application file for complete search history.

(56) References Cited

U.S. PATENT DOCUMENTS 5,833,956 A * 11/1998 Gorlin ................... A61K 8/442
424/49
2016/0136081 A1* 5/2016 Reierson ................. C07F 9/572
424/53

FOREIGN PATENT DOCUMENTS

EP 0422803 * 9/1990 ............... A61K 7/16

OTHER PUBLICATIONS

Rautemaa et al., "Oral infections and systemic disease—an emerging problem in medicine." Clin Microbiol Infect 2007;13:1041-1047 (Year: 2007).*

* cited by examiner

*Primary Examiner* — Walter E Webb
(74) *Attorney, Agent, or Firm* — Jarrod N. Raphael; Sarah Klosek

(57) ABSTRACT

An oral care composition including an amphoteric surfactant or betaine, a copolymer, and an orally acceptable cationic antibacterial agent; and methods of using the oral care composition.

20 Claims, No Drawings

ORAL CARE COMPOSITION

CROSS-REFERENCE TO RELATED APPLICATION

The present application claims the benefit of priority under 35 U.S.C. § 119(e) of U.S. Provisional Application Ser. No. 62/857,425, filed on Jun. 5, 2019, the entire disclosure of which is incorporated herein by reference.

TECHNICAL FIELD

The present disclosure relates to oral care compositions and methods of using such compositions. The present disclosure particularly relates to an oral care composition including an amphoteric surfactant or betaine, a copolymer, and an orally acceptable cationic antibacterial agent, and methods of using the oral composition.

BACKGROUND

Teeth are subject to various diseases and problems, among which are caries, plaque, tartar, gingivitis, abusive whitening practices from use of concentrated hydrogen peroxide, hypersensitivity, and enamel staining.

Most oral care diseases originate with the thin proteinaceous film deposited as pellicle onto tooth surfaces. This serves as a substrate for bacteria and mineral deposits which harden into plaque and eventually tartar. The bacterial colonies sheltered therein absorb and metabolize nutrients from substances that pass through the oral cavity, particularly sucrose, and produce carboxylic acids. These acids are not readily rinsed away by the oral fluids because the colonies are protected and held in close proximity to the tooth surfaces by the plaque film. The acids produced, then, are held against the dental surfaces, where they slowly demineralize and destroy the hydroxyapatite crystal structure, producing caries. The calculus and tartar deposits cause separation of the gingival tissue from the tooth, causing inflammation and creating "pockets" which also provide a more sheltered, difficult to clean area for the destructive process. The receding gingiva eventually exposes the dentinal tubules, which results in hypersensitivity.

Antimicrobial or antibacterial agents have been used in dental or oral care formulation to suppress bacterial activities in the oral cavity. However, some of these agents cause staining or yellowing of enamel in teeth. Accordingly, there remains a need for improved oral care formulations such as for preventing bacterial growth in the teeth or oral space and tooth staining.

SUMMARY

Provided herein, inter alia, are an oral care composition (e.g., oral care product) and a method using the same.

In one aspect, provided is an oral care composition that includes an orally acceptable carrier, an amphoteric surfactant; an orally acceptable cationic antibacterial agent; a copolymer (e.g., an anionic copolymer).

The amphoteric surfactant has a structure of formula (I):

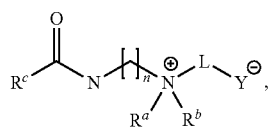
(I)

wherein L is a substituted or unsubstituted ($C_2$-$C_4$) alkylene,
n is an integer from 1 to 10,
$R^a$ and $R^b$ are independently $C_1$-$C_4$ alkyl,
$R^c$ is substituted or unsubstituted $C_1$-$C_{20}$ alkyl, and
Y is an anionic group.

The copolymer is a copolymer of:
i) an allyl phosphate compound; and ii) one or more α, β-ethylenically unsaturated co-monomers, at least one of which is other than an allyl-functional co-monomer. The allyl phosphate compound has the formula (A):

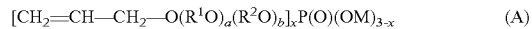
(A)

wherein
$R^1$ is a substituted or unsubstituted ($C_2$-$C_4$) alkylene moiety;
$R^2$ is a substituted or unsubstituted ($C_2$-$C_4$) alkylene moiety;
M is identical or different, hydrogen, alkali metal, ammonium, protonated alkyl amine, protonated alkanolamine, or protonated basic amino acid;
X is 1 or 2; a is from 1 to 20; and b is from 0 to 20.

In some embodiments, Y is —C(O)O, or —S(O)$_2$O. In some embodiments, n is 2, 3, or 4. In some embodiments, $R^a$ and $R^b$ are independently methyl or ethyl.

In some embodiments, the amphoteric surfactant is selected from the group consisting of cocamidopropyl betaine, lauramidopropyl betaine, cocobetaine, cocamidopropyl hydroxysultaine, and combinations thereof.

In some embodiments, $R^1$ and $R^2$ are independently substituted with a hydroxyl, alkoxyl, or aryloxyl moiety.

In some embodiments, the one or more α, β-ethylenically unsaturated co-monomers comprise a moiety selected from the group consisting of maleic anhydride, maleic acid, itaconic anhydride, itaconic acid, and combinations thereof.

In some embodiments, the orally acceptable cationic antibacterial agent is selected from the group consisting of chlorhexidine gluconate, cetyl pyridium chloride, quaternary ammonium surfactants, cationic amino acids, metal cations, and combinations thereof.

In some embodiments, the copolymer is polymerized from a mixture comprising one or more α, β-ethylenically unsaturated maleimide phosphate co-monomers, and the one or more α, β-ethylenically unsaturated co-monomers.

In some embodiments, one of the α, β-ethylenically unsaturated maleimide phosphate co-monomer has the formula (B),

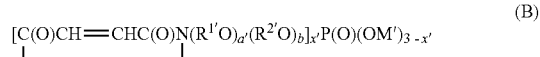
(B)

wherein
$R^{1'}$ is a substituted or unsubstituted ($C_2$-$C_4$) alkylene moiety;
$R^{2'}$ is a substituted or unsubstituted ($C_2$-$C_4$) alkylene moiety;
M' is identical or different, hydrogen, alkali metal, ammonium, protonated alkyl amine, protonated alkanolamine, or protonated basic amino acid;
X' is 1 or 2;
a' is from 1 to 20; and
b' is from 0 to 20.

In some embodiments, $R^{1'}$ and $R^{2'}$ are each independently substituted with a hydroxyl, alkoxyl, or aryloxyl moiety.

In some embodiments, one of the α, β-ethylenically unsaturated co-monomers has the formula (E):

(E)

wherein
$R^{2''}$ is H or an alkyl radical;
$R^{3''}$ is a linear or branched divalent aliphatic radical which may be hydroxyl substituted; and M" is alkali metal, ammonium, protonated alkyl amine, protonated alkanolamine, or protonated basic amino acid.

In some embodiments, the one or more of the α, β-ethylenically unsaturated co-monomers are selected from the group consisting of allyl ethoxylate, allyl polyethoxylate, methallyl ethoxylate, methallyl polyethoxylate, sodium 1-allyloxy-2-hydroxypropyl sulfonate, sodium 2-acrylamido-2-methylpropane sulfonate, sodium vinyl sulfonate, sodium styrene sulfonate, acrylic acid, methacrylic acid, vinyl acetate, acrylate ester, methacrylate ester, maleate ester, styrene, and combinations thereof.

In some embodiments, one of the α,β-ethylenically unsaturated co-monomers is a maleimide phosphate compound having a structure of

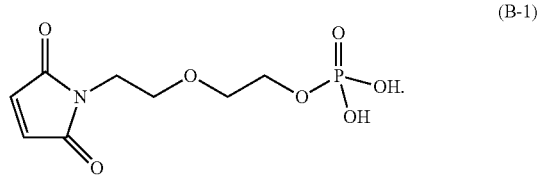 [SMILES: O=C1C=CC(=O)N1CCOCCOP(=O)(O)O]

(B-1)

In some embodiments, the allyl phosphate compound is of the formula (A-1)

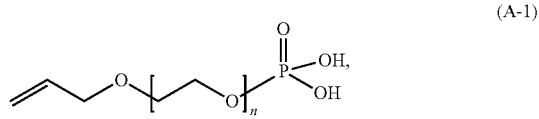

(A-1)

wherein n' is 1 to 20.

In some embodiments, the oral care composition further includes an abrasive polishing material selected from the group consisting of a silica, an alumina, an orthophosphate, a polyphosphate, a hexametaphosphate, and combinations thereof.

In some embodiments, the oral care composition further includes one or more additives selected from the group consisting of a polishing agent, a sudsing agent, a binder, a humectant, a medicinal agent, a sweetening agent, a flavor, a peroxide source, an alkali metal bicarbonate salt, a thickening agent, xylitol, sorbitol, a coloring agent, sodium carbonate, and combinations thereof.

The oral care composition may be in a form of a toothpaste, tooth gel, dentifrice, tooth powder, prophy paste, mouthwash, rinse, tooth mousse, dental floss, chewing gum, soluble oral care strip or film for direct application or attachment to an oral surface, or lozenge.

In one aspect, provided is a method of combating dental caries, erosion, hypersensitivity, and/or staining comprising using the oral care composition as described herein.

In another aspect, provided is a method of treating or preventing dental caries, erosion, hypersensitivity, and/or staining comprising using the oral care composition as described herein.

Other aspects of the invention are disclosed infra.

DETAILED DESCRIPTION

Definitions

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

While compositions and methods are described in terms of "comprising," "containing," or "including" various components or steps, the compositions and methods can also "consist essentially of" or "consist of" the various components, substances and steps. As used herein the term "consisting essentially of" shall be construed to mean including the listed components, substances or steps and such additional components, substances or steps which do not materially affect the basic and novel properties of the composition or method. In some embodiments, a composition in accordance with embodiments of the present disclosure that "consists essentially of" the recited components or substances does not include any additional components or substances that alter the basic and novel properties of the composition.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The terms "a" or "an," as used in herein means one or more. For example, the phrase "substituted with a[n]," as used herein, means the specified group may be substituted with one or more of any or all of the named substituents. For example, where a group, such as an alkyl group, is "substituted with an unsubstituted $C_1$-$C_{20}$ alkyl," the group may contain one or more unsubstituted $C_1$-$C_{20}$ alkyls.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

A charged moiety refers to a functional group possessing an abundance of electron density (i.e. electronegative or negatively charged) or is deficient in electron density (i.e. electropositive or positively charged). Non-limiting examples of a charged moiety includes carboxylic acid, alcohol, phosphate, aldehyde, and sulfonamide. In embodiments, a charged moiety is capable of forming hydrogen bonds or ionic bonds.

The term "solution" is used in accor and refers to a liquid mixture in which the minor component (e.g., a solute or compound) is uniformly distributed within the major component (e.g., a solvent).

As used herein, the term "salt" refers to acid or base salts of the compounds used in the methods described herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "silica" is used according to its plain and ordinary meaning and refers to a composition (e.g. a solid composition such as a crystal, nanoparticle, or nanocrystal) containing oxides of silicon such as Si atoms (e.g., in a tetrahedral coordination) with 4 oxygen atoms surrounding a central Si atom. Nanoparticles may be composed of at least two distinct materials, one material (e.g., insoluble drug) forms the core and the other material forms the shell (e.g., silica) surrounding the core; when the shell includes Si atoms, the nanoparticle may be referred to as a silica nanoparticle. A silica nanoparticle may refer to a particle including a matrix of silicon-oxygen bonds wherein the longest diameter is typically less than or equal to 1000 nanometers.

A functionalized silica nanoparticle, as used herein, may refer to the post hoc conjugation (i.e. conjugation after the formation of the silica nanoparticle) of a moiety to the hydroxyl surface of a nanoparticle. For example, a silica nanoparticle may be further functionalized to include additional atoms (e.g., nitrogen) or chemical entities (e.g., polymeric moieties or bioconjugate group). For example, when the silica nanoparticle is further functionalized with a nitrogen containing compound, one of the surface oxygen atoms surrounding the Si atom may be replaced with a nitrogen containing moiety.

The term "polymeric" refers to a molecule including repeating subunits (e.g., polymerized monomers). For example, polymeric molecules may be based upon polyethylene glycol (PEG), poly[amino(1-oxo-1,6-hexanediyl)], poly(oxy-1,2-ethanediyloxycarbonyl-1,4-phenylenecarbonyl), tetraethylene glycol (TEG), polyvinylpyrrolidone (PVP), poly(xylene), or poly(p-xylylene). See, for example, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA, which are incorporated by reference in their entirety for all purposes.

The phrase "average molecular weight" refers to the weight average molecular weight of a polymer as determined by gel permeation chromatography (also known as GPC or size exclusion chromatography (SEC)) using tetrahydrofuran (THF) water pH 7 buffered solution as the solvent and using light scattering detection.

If there is any conflict in the usages of a word or term in this specification and one or more patent or other documents that may be incorporated herein by reference, the definitions that are consistent with this specification should be adopted.

Oral Care Compositions

While some exemplary embodiments are discussed, the specification is illustrative only and not restrictive. Many variations of this disclosure will become apparent to those skilled in the art upon review of this specification.

In an aspect, provided is an oral care composition. The oral care composition may be or be included in an oral care product, which may be in a form of, but is not limited to, a toothpaste, tooth gel, dentifrice, tooth powder, prophy paste, mouthwash, rinse, tooth mousse, dental floss, chewing gum, soluble oral care strip or film for direct application or attachment to an oral surface, or lozenge.

The oral care composition includes an orally acceptable carrier; an amphoteric surfactant; an orally acceptable cationic antibacterial agent; and a copolymer (e.g., anionic copolymer).

The amphoteric surfactant may be a betaine compound. The term "betaine" as used herein refers to any compound that is neutral overall but has both a cationic functional moiety and an anionic functional moiety. In an exemplary embodiment, the amphoteric surfactant or the betaine includes a quaternary ammonium cation (positively charged group) and a carboxylic anion (negatively charged group). In an exemplary embodiment, the amphoteric surfactant or the betaine includes a quaternary ammonium cation (positively charged group) and a sulfite anion (negatively charged group). In an exemplary embodiment, the amphoteric surfactant or the betaine includes a quaternary ammonium cation (positively charged group) and a sulfate anion (negatively charged group). In an exemplary embodiment, the amphoteric surfactant or the betaine includes a quaternary ammonium cation (positively charged group) and a phosphate anion (negatively charged group).

The amphoteric surfactant has a structure of formula (I):

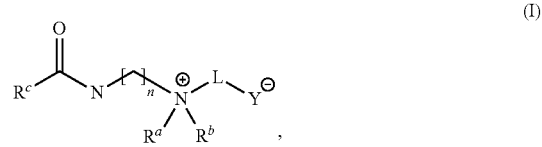

(I)

wherein L is a substituted or unsubstituted ($C_2$-$C_4$) alkylene;
n is an integer from 1 to 10;
$R^a$ and $R^b$ are independently $C_1$-$C_4$ alkyl;
$R^c$ is substituted or unsubstituted $C_1$-$C_{20}$ alkyl; and
Y is an anionic group.

In some embodiments, Y is —C(O)O, or —S(O)₂O. In an exemplary embodiment, Y is —C(O)O. In an exemplary embodiment, Y is —S(O)₂O.

In some embodiments, n is 2, 3, or 4. In an exemplary embodiment, n is 2. In an exemplary embodiment, n is 3. In an exemplary embodiment, n is 4.

In some embodiments, $R^a$ and $R^b$ are independently methyl or ethyl. In an exemplary embodiment, $R^a$ is methyl. In an exemplary embodiments, $R^a$ is ethyl. In an exemplary embodiment, $R^b$ is methyl. In an exemplary embodiment, $R^b$ is ethyl.

In some embodiments, L is unsubstituted $(C_2-C_4)$ alkylene. In an exemplary embodiment, L is ethylene. In an exemplary embodiment, L is propylene. In an exemplary embodiment, L is isopropylene. In an exemplary embodiment, L is butylene. In an exemplary embodiment, L is isobutylene. In an exemplary embodiment, L is t-butylene.

In some embodiments, L is substituted $(C_2-C_4)$ alkylene. In an exemplary embodiment, L is OH-substituted $(C_2-C_4)$ alkylene. In an exemplary embodiment, L is OH-substituted ethylene. In an exemplary embodiment, L is OH-substituted propylene. In an exemplary embodiment, L is OH-substituted isopropylene. In an exemplary embodiment, L is OH-substituted butylene. In an exemplary embodiment, L is OH-substituted isobutylene. In an exemplary embodiment, L is OH-substituted t-butylene.

In some embodiments, $R^c$ is unsubstituted $C_1-C_{20}$ alkyl. In an exemplary embodiment, R is unsubstituted $C_4-C_{20}$ alkyl. In an exemplary embodiment, $R^c$ is unsubstituted $C_4-C_{12}$ alkyl. In an exemplary embodiment, $R^c$ is unsubstituted $C_8-C_{12}$ alkyl. In an exemplary embodiment, $R^c$ is unsubstituted $C_8$ alkyl. In an exemplary embodiment, $R^c$ is unsubstituted $C_9$ alkyl. In an exemplary embodiment, $R^c$ is unsubstituted $C_{10}$ alkyl. In an exemplary embodiment, $R^c$ is unsubstituted $C_{11}$ alkyl. In an exemplary embodiment, $R^c$ is unsubstituted $C_{12}$ alkyl.

In some embodiments, the amphoteric surfactant has a structure of

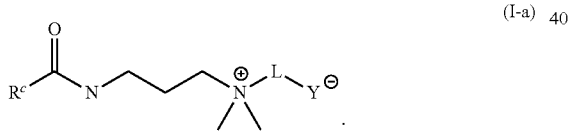
(I-a)

In some embodiments, the amphoteric surfactant has a structure of

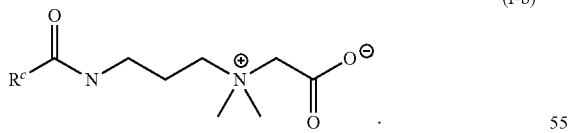
(I-b)

In some embodiments, the amphoteric surfactant has a structure of

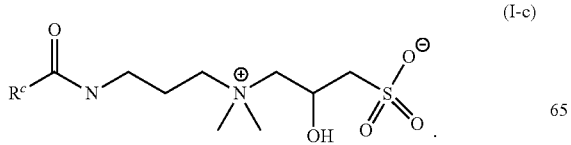
(I-c)

In some embodiments, the amphoteric surfactant is selected from cocamidopropyl betaine, lauramidopropyl betaine, cocobetaine, cocamidopropyl hydroxysultaine, and combinations thereof. In some embodiments, the amphoteric surfactant is selected from cocamidopropyl betaine, lauramidopropyl betaine, cocobetaine, cocamidopropyl hydroxysultaine, and combinations thereof.

The orally acceptable cationic antibacterial agent may include an agent which exists as a cation in aqueous solution at a physiological pH (e.g., pH ranging about from 6.5 to 7.8, from 7.0 to 7.5, or from 7.35 to 7.45) and which provides a particular benefit, e.g., reducing or suppressing microbial activity in the physiological environment or surroundings. For example, the cationic antibacterial agent may provide anti-gingivitis, anticavity and/or antierosion activity to the teeth, gums, or oral cavity. The cationic antibacterial agent may be soluble, or substantially soluble in the aqueous solution (e.g., water, saliva, or a solution of the oral care product). In some embodiments, the cationic antibacterial agent may be introduced to the formulation formulated in free or salt form.

In some embodiments, the cationic antibacterial agent may be selected from one or more of quaternary ammonium surfactants (e.g., cetyl pyridinium chloride (CPC)), bisguanides (e.g., chlorhexidine digluconate), cationic amino acids (e.g., arginine), metal cations (e.g., zinc (Zn), calcium (Ca), or stannous (Sn) ions), or combinations thereof. In some embodiments, the cationic antibacterial agents can cause or enhance staining, for example, due to the deposit of chromogens or salt forms thereof.

The copolymer includes, or is made of: i) an allyl phosphate compound; and ii) one or more α, β-ethylenically unsaturated co-monomers, at least one of which is other than an allyl-functional co-monomer.

The allyl phosphate compound has the formula (A):

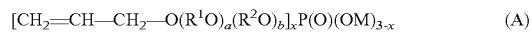
(A)

wherein
$R^1$ is a substituted or unsubstituted $(C_2-C_4)$ alkylene moiety;
$R^2$ is a substituted or unsubstituted $(C_2-C_4)$ alkylene moiety;
M is identical or different, hydrogen, alkali metal, ammonium, protonated alkyl amine, protonated alkanolamine, or protonated basic amino acid;
X is 1 or 2,
a is from 1 to 20; and
b is from 0 to 20.

In some embodiments, $R^1$ and $R^2$ are independently substituted with a hydroxyl, alkoxyl, or aryloxyl moiety.

In an exemplary embodiment, the allyl phosphate compound of formula (A) can be prepared by various methods. For example, U.S. Pat. No. 8,653,181, incorporated herein by reference in its entirety, describes methods for preparing allyl ethoxylate phosphate ester embodiments of formula (A).

The α, β-ethylenically unsaturated co-monomers may be any such compound but preferably monomers that copolymerize well with allyl monomers and may include those different from monomer (A) but still contain phosphate or other functional groups, such as carboxylate, or sulfonate. In some embodiments, one or more of the α, β-ethylenically unsaturated co-monomers is an allyl functional sulfonate monomer such as, for example, sodium 1-allyloxy-2-hydroxypropyl sulfonate or a non-allyl monomer, sodium 2-acrylamido-2-methylpropane sulfonate, sodium vinyl sulfonate, sodium styrene sulfonate, acrylic acid or methacrylic acid, maleic acid, maleic anhydride (optionally, as its anhydride that is hydrolyzed post-polymerization), fumaric acid, itaconic acid and their water soluble salts, particularly their alkali metal or ammonium salts, as described in U.S. Pat. No. 9,115,236, incorporated herein by reference.

In some embodiments, the allyl phosphate compound (A) has a structure of formula (A-1).

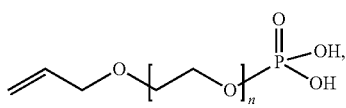

(A-1)

wherein n is 1 to 20.

In some embodiments, n' is 1 to 10. In an exemplary embodiment, n' is 2 to 8. In an exemplary embodiment, n' is 3 to 6. In an exemplary embodiment, n' is 3 to 5. In an exemplary embodiment, n' is 3 or 4.

In some embodiments, one or more of the α, β-ethylenically unsaturated co-monomers is an allyl ethoxylate or methallyl ethoxylate. In some embodiments, one or more of the α, β-ethylenically unsaturated co-monomers is a compound according to formula (B), which is described below. In some embodiments, one or more of the α, β-ethylenically unsaturated co-monomers is selected from combinations of any of the above-mentioned co-monomers.

In some embodiments, one or more α, β-ethylenically unsaturated co-monomers include a moiety selected from maleic anhydride, maleic acid, itaconic anhydride, itaconic acid, and combinations thereof. In an exemplary embodiment, one or more α, β-ethylenically unsaturated co-monomers include a maleic anhydride moiety. In an exemplary embodiment, one or more α, β-ethylenically unsaturated co-monomers include a maleic acid moiety. In an exemplary embodiment, one or more α, β-ethylenically unsaturated co-monomers include an itaconic anhydride moiety. In an exemplary embodiment, one or more α, β-ethylenically unsaturated co-monomers include an itaconic acid moiety.

In some embodiments, one or more of the α, β-ethylenically unsaturated co-monomers include, or is an α, β-ethylenically unsaturated maleimide phosphate compound of the formula (B):

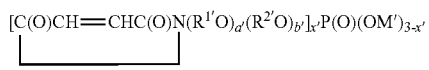

(B)

wherein
$R^{1'}$ is a substituted or unsubstituted ($C_2$-$C_4$) alkylene moiety;
$R^{2'}$ is a substituted or unsubstituted ($C_2$-$C_4$) alkylene moiety;
M' is identical or different, hydrogen, alkali metal, ammonium, protonated alkyl amine, protonated alkanolamine, or protonated basic amino acid;
X' is 1 or 2,
a' is from 1 to 20; and
b' is from 0 to 20.

In some embodiments, $R^{1'}$ and $R^{2'}$ in the compound of formula (B) are independently substituted with a hydroxy, alkoxy or aryloxy moiety.

In some embodiments, the copolymer is polymerized from a mixture (e.g., monomer mixtures) including the allyl phosphate compound, and one or more α, β-ethylenically unsaturated co-monomers. In some embodiments, the copolymer is polymerized from a mixture (e.g., monomer mixtures) including the allyl phosphate compound, and one or more α, β-ethylenically unsaturated co-monomers (e.g., one or more α, β-ethylenically unsaturated maleimide phosphate co-monomers). In some embodiments, the copolymer is polymerized from a mixture (e.g., monomer mixtures) including the allyl phosphate compound, one or more α, β-ethylenically unsaturated co-monomers, and the one or more α, β-ethylenically unsaturated maleimide phosphate co-monomers. In some embodiments, the copolymer is polymerized from a mixture (e.g., monomer mixtures) including the allyl phosphate compound, and one or more α, β-ethylenically unsaturated maleimide phosphate co-monomers. In some embodiments, the copolymer is polymerized from a mixture (e.g., monomer mixtures) including one or more α, β-ethylenically unsaturated co-monomers, and one or more α, β-ethylenically unsaturated maleimide phosphate co-monomers.

The α, β-ethylenically unsaturated maleimide phosphate compound of formula (B) can be prepared by several processes. In an embodiment, 2-hydroxyethyl-2-oxyethyl amine (Diglycolamine, available from Huntsman Corporation) is reacted with an approximately equimolar amount of maleic anhydride in chloroform according to an altered version of the method described in Example 1 of U.S. Pat. No. 2,980,652, with Diglycolamine substituted for the 1-(2-aminoethyl)imadazolidinone-2 used in the example. The resultant compound is then ring closed according to an altered method of Example 5 of U.S. Pat. No. 2,980,652. In the altered version of the method, the resultant compound contains —$CH_2CH_2OCH_2CH_2OH$ in place of the imidazolidinone-2 ring in the formula at lines 40-44 of Column 10 of the '652 patent. The resultant ring-closed hydroxy-functional maleimide compound is then phosphated by reacting it with polyphosphoric acid and phosphoric anhydride according to an altered method of Example 1 of U.S. Pat. No. 5,550,274, with the hydroxy-functional maleimide compound substituted for the lauryl alcohol and adjusting the molar amount of the phosphation reagent to the specific requirements of the process.

In some embodiments the maleimide phosphate compound of formula (B) is a compound of formula (B-1):

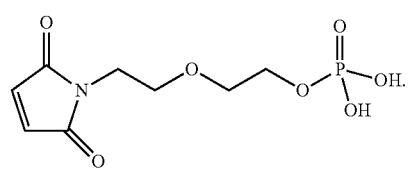

(B-1)

In some embodiments, the copolymer may be polymerized from a monomer mixture including one or more α, β-ethylenically unsaturated maleimide phosphate compounds of formula (B) and one or more α, β-ethylenically unsaturated co-monomers, at least one of which is other than a maleimide-functional co-monomer.

In some embodiments, one or more of the α, β-ethylenically unsaturated co-monomers polymerized with one or more compounds of formula (B) is an allyl functional sulfonate monomer such as, for example, sodium 1-allyloxy-2-hydroxypropyl sulfonate or a non-allyl monomer, sodium 2-acrylamido-2-methylpropane sulfonate, sodium vinyl sulfonate, sodium styrene sulfonate, acrylic acid or methacrylic acid, maleic acid, maleic anhydride (optionally, as its anhydride that is hydrolyzed post-polymerization), fumaric acid, itaconic acid and their water soluble salts, particularly their alkali metal or ammonium salts, as described in U.S. Pat. No. 9,115,236, incorporated herein by reference. In some embodiments, one or more of α, β-ethylenically unsaturated co-monomers may include allyl ethoxylate (or polyethoxylate) or methallyl ethoxylate (or polyethoxylate). In some embodiments, one or more of the α, β-ethylenically unsaturated co-monomers may be a compound according to formula (A), which is described above.

In some embodiments, the one or more of the α, β-ethylenically unsaturated co-monomers are selected from allyl ethoxylate, allyl polyethoxylate, methallyl ethoxylate, methallyl polyethoxylate, sodium 1-allyloxy-2-hydroxypropyl sulfonate, sodium 2-acrylamido-2-methylpropane sulfonate, sodium vinyl sulfonate, sodium styrene sulfonate, acrylic acid, methacrylic acid, vinyl acetate, acrylate ester, methacrylate ester, maleate ester, styrene, and combinations thereof. In some embodiments, the one or more of α, β-ethylenically unsaturated co-monomers may include one or more selected from combinations of any of the above-mentioned co-monomers.

In some embodiments, the copolymer has a molecular weight and functionality selected so that the copolymer forms a film which protects a dental surface from attachment of bacteria, plaque, and staining agents while enhancing the deposition and retention of fluoride, anti-bacterial agents and/or gentle tooth whiteners onto the dental surface.

Although the acidic, ionic monomers may be copolymerized in either the acid or salt form, it is understood that it would be necessary to adjust the pH of the final copolymer to physiological pH (e.g., pH ranging about from 6.5 to 7.8, from 7.0 to 7.5, or from 7.35 to 7.45), hence at least partially converting the acidic groups to the salt forms.

In some embodiments, co-monomers as used herein are selected and the polymerization process chosen to maximize incorporation of the monomers into the copolymer according to the desired distribution: random, alternating or in blocks. In some aspects, the "-mer" units are distributed as evenly as possible along the polymer chain.

In some embodiments, non-ionic monomers are used to balance the reactivities of the selected monomer mixtures and influence bulk properties of the copolymer, such as water solubility, $T_g$, toughness, durability or cost. These would include vinyl acetate, acrylate esters, methacrylate esters, maleate esters and diesters, fumarate diesters and styrene. In some embodiments, the copolymer may further include one or more non-ionic monomers.

For example, at least one of the co-monomers is a non-ionic maleimidoalkoxylate co-monomer compound of formula (C):

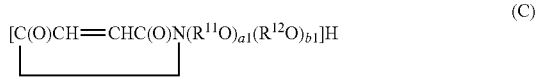

(C)

wherein
R$^{11}$ is a substituted or unsubstituted (C$_2$-C$_4$) alkylene moiety;
R$^{12}$ is a substituted or unsubstituted (C$_2$-C$_4$) alkylene moiety;
a1 is from 1 to 20; and
b1 is from 0 to 20.

In some embodiments, R$^{11}$ and R$^{12}$ in the formula (C) are each independently (C$_2$-C$_4$) alkylene moiety substituted with a hydroxy, alkoxy or aryloxy moiety.

An example of a suitable non-ionic maleimide alkoxylate comonomer compound is of the formula (C-1):

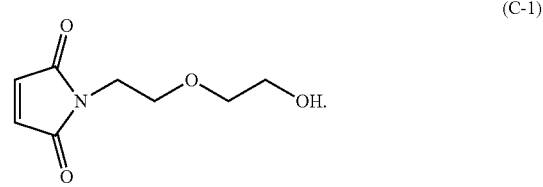

(C-1)

The maleimide derivatives may be prepared by reacting the proper primary amine with maleic anhydride as reported in U.S. Pat. No. 5,306,828. The monomer (C-1) can be set aside from the bulk of the maleimide for later use or a portion of the total charge could be phosphated with a reduced phosphation reagent charge, leaving excess (C-1) in the phosphate product mixture as a "non-ionic" monomer of similar polymerization reactivity and a terminal hydroxyl group compatible with the other comonomers. It would serve as a "diluent" monomer that could reduce the phosphate monomer content in the copolymer if that were desired.

In some embodiments, the copolymer (e.g., terpolymers) including additional ethylenically unsaturated monomers and the allyl alkoxylate phosphate esters of formula (A) and/or maleimide polyalkoxylate phosphate esters of formula (B) can be prepared by synthesis methods described in U.S. Pat. No. 9,115,236.

In some embodiments, one or more of the α, β-ethylenically unsaturated co-monomers polymerized with one or more compounds of formula (B) is an allyl functional sulfonate monomer such as, for example, sodium 1-allyloxy-2-hydroxypropyl sulfonate or a non-allyl monomer, sodium 2-acrylamido-2-methylpropane sulfonate, sodium vinyl sulfonate, sodium styrene sulfonate, acrylic acid or methacrylic acid, maleic acid, maleic anhydride (optionally, as its anhydride that is hydrolyzed post-polymerization), fumaric acid, itaconic acid and their water soluble salts, particularly their alkali metal or ammonium salts, as described in U.S. Pat. No. 9,115,236, incorporated herein by reference. In some embodiments, one or more of the α, β-ethylenically unsaturated co-monomers is allyl ethoxylate (or polyethoxylate) or methallyl ethoxylate (or polyethoxylate). In some embodiments, one or more of the α, β-ethylenically unsaturated co-monomers is a compound according to formula (A), which is described above. In some embodiments, one or more of the α, β-ethylenically unsaturated co-monomers is selected from combinations of any of the above-mentioned co-monomers.

In some embodiments, non-ionic monomers are used to balance the reactivities of the selected monomer mixtures and influence bulk properties of the copolymer, such as water solubility, $T_g$, toughness, durability or cost. Suitable non-ionic monomers include, for example, vinyl acetate, acrylate esters, methacrylate esters, maleate esters and diesters, fumarate diesters, and styrene.

Although the acidic, ionic monomers may be copolymerized in either the acid or salt form, it is understood that it would be necessary to adjust the pH of the final copolymer to physiological pH, hence at least partially converting the acidic groups to the salt forms.

In some embodiments, the co-monomers are selected so that the copolymer is an alternating copolymer having essentially no homopolymerization. In some embodiments, the co-monomers are selected so that the copolymer is an alternating copolymer exhibiting a degree of homopolymerization.

In some embodiments, one or more of the α, β-ethylenically unsaturated co-monomers is one or more allyl functional monomers, which may be homologues of the polyalkylene oxide monoallyl ether starting materials for formula (A). The allyl functional monomer has a formula (D):

$$[CH_2=CH-CH_2-O(R_1O)_a(R_2O)_b]_xH \quad (D),$$

wherein $R_1$, $R_2$, a, b, and X are defined as in formula (A).

In some embodiments the α, β-ethylenically unsaturated phosphate co-monomer, is an allyl compound of formula (D-1):

$$CH_2=CH-CH_2-O(CH_2CH_2O)_a-H \quad (D-1)$$

wherein a is 1 to 20.

In some embodiments, one or more of the α, β-ethylenically unsaturated co-monomers is an allyl functional monomer of the formula (E):

$$CH_2=C(R^{2''})CH_2O(R^{3''})(OH)SO_3M'' \quad (E)$$

wherein
$R^{2''}$ is H or an alkyl radical;
$R^{3''}$ is a linear or branched substituted or unsubstituted divalent aliphatic radical; and
M" is alkali metal, ammonium, protonated alkyl amine, protonated alkanolamine, or protonated basic amino acid.

In some embodiments, one or more of the α, β-ethylenically unsaturated co-monomers is selected from combinations of any of the above-mentioned co-monomers.

Also presented are oral care compositions that include one or more of any of the phosphate copolymers according to the present disclosure. Compositions according to the present disclosure are suitable for use by human and nonhuman mammals. The term "oral care composition" as used herein means a product that in the ordinary course of usage is retained in the oral cavity for a time sufficient to contact some or all of the dental surfaces and/or oral tissues for purposes of oral activity. The term "dental surface" as used herein means a surface of a natural tooth or a hard surface of artificial dentition including a denture, dental plate, crown, cap, filing, bridge, dental implant, and the like.

In some embodiments, the oral care composition is selected from toothpastes, tooth gels, dentifrices, tooth powders, prophy pastes, mouthwashes, rinses, tooth mousse, dental floss, chewing gum, soluble oral care strips or films for direct application or attachment to oral surfaces, or lozenges. In some embodiments, the oral care composition includes at least one copolymer having a molecular weight and functionality selected so that the copolymer forms a film that adheres to and protects a dental surface from acidic beverage or acid-reflux induced erosion, hypersensitivity, attachment of bacteria, plaque, and staining agents while enhancing the deposition and retention of fluoride, antibacterial agents, or gentle whitening agents onto the dental surface.

In some embodiments, the oral care composition includes an orally acceptable carrier. In various embodiments, the carrier is a liquid, semi-solid, or solid. A "liquid" can be a liquid of low or high viscosity. A liquid can be a liquid such that flow is imperceptible under ambient conditions. A liquid can be a thixotropic liquid. A "semi-solid" as used herein can be a gel, a colloid, or a gum. As used herein, semi-solids and liquids are fluids distinguished on the basis of viscosity: a semi-solid is a high viscosity fluid, while a liquid has lower viscosity. There is no definitive dividing line between these two types of fluids. A semi-solid can, in certain embodiments, have a viscosity as high as thousands of mPas. Carriers among those useful herein include liquids, pastes, ointments, and gels, and can be transparent, translucent or opaque. In some embodiments, the orally acceptable carrier includes water. For instance, the one or more of the copolymers are present, for example, as being soluble, in a liquid carrier.

In some embodiments, the oral care composition includes an abrasive polishing material. In some embodiments, the abrasive polishing material is selected from a silica, an alumina, an orthophosphate, a polyphosphate, a hexametaphosphate, and combinations thereof. In some embodiments, the oral care composition includes an abrasive agent selected from one or more of hydrated silica, colloidal silica, fumed silica, and combinations thereof. In some embodiments, the oral care composition includes insoluble sodium hexametaphosphate, insoluble sodium aluminosilicates, sodium bicarbonate and combinations thereof.

In some embodiments, the oral care composition includes one or more additives. In some embodiments, one or more additives are selected from a polishing agent, a sudsing agent, a binder, a humectant, a medicinal agent, a sweetening agent, a flavor, a peroxide source, an alkali metal bicarbonate salt, a thickening agent, xylitol, sorbitol, a coloring agent, sodium carbonate, and combinations thereof.

In some embodiments, the oral care composition includes a safe and effective amount of a fluoride source. The fluoride source may be sufficient to provide anticaries effectiveness. A wide variety of fluoride ion-yielding materials can be employed as sources of soluble fluoride in the present oral care compositions. Representative fluoride ion sources include: sodium fluoride, potassium fluoride, sodium monofluorophosphate, and combinations thereof.

In some embodiments, the oral care composition further includes a phosphate ester surfactant. Suitable phosphate ester surfactants include those described in U.S. Pat. No. 9,040,025, the disclosure of which is incorporated herein by reference in its entirety.

In some embodiments, the oral care composition is a tooth cleaning product, which includes one or more copolymers and an amphoteric surfactant (betaine) as described herein. In some embodiments, the tooth cleaning product further includes an abrasive agent. In some embodiments, the tooth cleaning product is free of calcium and other divalent ions, a surfactant, a phosphate ester salt, and optionally a liquid.

Also provided are methods of combating dental caries, erosion, hypersensitivity, and/or staining using the oral care composition as described herein. The method of use herein includes contacting a subject's dental surfaces and/or oral mucosa with the oral care compositions according to the present disclosure. In some embodiments, the oral care composition is deposited as a protective film. The method of treatment may be by brushing and/or rinsing. Other methods include contacting the toothpaste, tooth gel, dentifrice, tooth powder, prophy paste, mouthwash, rinse, tooth mousse, dental floss, chewing gum, soluble oral care strips or films, or lozenges or other form with the subject's dental surfaces and/or oral mucosa. Depending on the embodiment, the oral care composition may be used as frequently as a toothpaste, or may be used less often, for example, weekly, or used by a professional in the form of a prophy paste or other intensive treatment.

Further provided is a method of treating or preventing dental caries, erosion, hypersensitivity, and/or staining comprising using the oral care composition as described herein. The method of use herein includes contacting a subject's dental surfaces and/or oral mucosa with the oral care compositions according to the present disclosure. In some embodiments, the oral care composition is deposited as a protective film. The method of treatment may be by brushing and/or rinsing. Other methods include contacting the toothpaste, tooth gel, dentifrice, tooth powder, prophy paste, mouthwash, rinse, tooth mousse, dental floss, chewing gum, soluble oral care strips or films, or lozenges or other form with the subject's dental surfaces and/or oral mucosa. Depending on the embodiment, the oral care composition may be used as frequently as a toothpaste, or may be used less often, for example, weekly, or used by a professional in the form of a prophy paste or other intensive treatment.

It should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

The present disclosure will further be described by reference to the following examples. The following examples are merely illustrative and are not intended to be limiting. Unless otherwise indicated, all percentages are by weight of the total composition.

EXAMPLES

Chlorhexidine gluconate ("CHX") is a cationic chemical used as an anti-microbial agent for treating periodontitis, gingivitis, and other oral care and gum diseases. While very effective as an anti-microbial agent its major side effect is yellowing or staining of the tooth enamel. An anionic polymer has been tested for stain prevention efficacy in dental application. However, the polymer is anionic and as such is incompatible with the cationic anti-microbial agent. It was observed that by adding an amphoteric surfactant such as lauramidopropyl betaine to the polymer, the anti-microbial agent was soluble in the blend. This blend was then tested for stain prevention efficacy and compared against a control containing just the chlorhexidine and amphoteric surfactant. It was observed that by adding the polymer/amphoteric blend with the chlorhexidine reduced the staining of the teeth significantly when compared with just the chlorhexidine and amphoteric solution.

Example 1: Co-Polymer Synthesis

Poly(Maleic Acid-co-PAM5000) ("P(MA-co-PAM-5000)")
In a 1 liter reactor equipped with a mechanical stirrer and condenser are introduced at room temperature 62.40 g of 43 wt. % aqueous maleic acid; 37.60 of 73.9 wt. % aqueous solution of SIPOMER PAM5000 (Solvay, CAS number 60497-09-08). After deoxygenation with nitrogen bubbling for 30 minutes, the mixture was brought to 80° C. with agitation. Then, 10 g of 25 wt. % aqueous solution of sodium persulfate was added. After 60 minutes of reaction, 10.03 g of 25 wt. % aqueous solution of sodium persulfate was added in one shot. The mixture was then held at 80° C. under agitation for 4 hours. After 6 hours total reaction time at 80° C., the mixture was cooled down to room temperature, and the mixture was neutralized with 34.1 g of 50 wt. % aqueous sodium hydroxide under agitation. The average molecular weight was 12,000 g/mol. The measured solid (120° C. for 60 min) was 51.48 wt. %.

Poly(Acrylic Acid-co-PAM5000) ("P(AA-co-PAM-5000)")
In a 1 liter reactor equipped with a mechanical stirrer and condenser, are introduced at room temperature 92.10 g of 29.4 wt. % aqueous solution of SIPOMER PAM5000 (Solvay, CAS number 60497-09-08); 211.92 g of purified water. After deoxygenation with nitrogen bubbling for 60 minutes, the mixture was brought to 80° C. over 60 minutes. The following was then added simultaneously over 180 minutes: 67.69 g of 39.3 wt. % aqueous solution of acrylic acid, and 17.10 g of 2.82 wt. % aqueous solution of sodium hypophosphite, and over 195 minutes 41.32 g of 10.06 wt. % aqueous solution of sodium persulfate was added. The mixture was then held at 80° C. under agitation for 1 hour. After 4 hours of total reaction time at 80° C. the mixture was cooled down to room temperature over 60 minutes, the mixture was then neutralized with 35.88 g of 50 wt. % aqueous solution of sodium hydroxide. The number average molecular weight was between 10,000-200,000 g/mol. The measure solid (115° C.; 60 min) was 15.24 wt. % Example 2: Blend formulation process The polymer/amphoteric blend were made in a 1:1 ratio. In a beaker water was measured and 0.5%-10% amphoteric surfactant (cocamidopropyl betaine; lauramidopropyl betaine; coco betaine; cocamidopropyl hydroxysultaine, etc.) was added and mixed. Next the 0.5%-10% polymer was added and mixed to form a uniform blend. Under agitation 0.12% chlorhexidine gluconate was accurately weighed and added to the beaker and allowed to mix until completely uniform and clear solution was obtained. The pH of the formulation was measured and adjusted to 5-8 (target 6.5).

Staining Prevention Protocol
Preparation of Artificial Saliva
1. Hydroxyapatite (HAP) disc are soaked in artificial saliva (Table 1) overnight to facilitate pellicle formation.
2. A solution was made of 1% polymer/amphoteric blend with 0.12% chlorhexidine gluconate in 0.3M salt solution; and 0.12% chlorhexidine in 1% amphoteric surfactant in 0.3M salt solution.
3. Each HAP disc was treated with 30 ml of one of the test solutions for 15 minutes. A L*a*b value was obtained using the colorflex EZ spectrophotometer. The HAP discs were then dipped in 30 ml 10% coffee/tea staining solution for one hour. They were then rinsed with DI water for 10 seconds and soaked in 30 ml artificial saliva for one hour. This cycle was repeated three times. At the end of the $3^{rd}$ cycle the L*a*b reading was recorded and the ΔL was calculated.

TABLE 1

| Artificial Saliva | |
|---|---|
| Ingredient | 1000 ml |
| Lab Lemco | 1 |
| Proteose Peptone | 5 |
| Yeast Extract | 2 |
| NaCl | 0.35 |
| $CaCl_2$ | 0.2 |

TABLE 1-continued

Artificial Saliva

| Ingredient | 1000 ml |
|---|---|
| KCl | 0.2 |
| Porcine Mucine Type II | 2.5 |
| 40% w/v Urea | 1.3 |
| Water | QS |

Protocol
1. Soak Hydroxyapatite disc (HAP) disc overnight in artificial saliva to facilitate pellicle formation,
2. Coat the HAP disc with 30 ml 1% test solution for 15 minutes,
3. Take the first L*a*b reading.
4. Soak the HAP disc in 30 ml 10% staining solution (5% coffee and 5% tea) for 60 min.
5. Rinse the HAP disc with water for 10 seconds.
6. Incubate the disc in 30 ml artificial saliva at 37° C. for 60 min.
7. Repeat steps 4-6 for 3 cycles.
8. At the end of $3^{rd}$ cycle take the final L*a*b reading and calculate the ΔL.
9. The % stain prevention is calculated using the following equation.

% Stain Inhibition={(ΔL treated/ΔL untreated)×100}−100

Example 3: Compatibility and Stain Prevention Data

TABLE 2

Compatibility:

| Sample | 0.1% CHX | 0.5% CHX |
|---|---|---|
| 1% P(AA-co-PAM5000) polymer (control - polymer is incompatible with CHX) | Precipitate | Precipitate |
| 1% P(MA-co-PAM5000) polymer (control - polymer is incompatible with CHX) | Precipitate | Precipitate |
| 1% Lauramidopropyl Betaine + 1% P(AA-co-PAM 5000) | Clear solution | Clear solution |
| 2% Lauramidopropyl Betaine + 2% P(AA-co-PAM 5000) | Clear solution | Clear solution |
| 1% Lauramidopropyl Betaine + 1% P(MA-co-PAM 5000) | Clear solution | Clear solution |
| 2% Lauramidopropyl Betaine + 2% P(MA-co-PAM 5000) | Clear solution | Clear solution |

(CHX = chlorhexidine gluconate)

TABLE 3

% Stain prevention

| Sample | % stain prevention |
|---|---|
| 1% Lauramidopropyl Betaine + 0.12% Chlorhexidine Gluconate (control - no polymer) | −26.0% |
| 1% Lauramidopropyl Betaine + 1% P(AA-co-PAM5000) + 0.12% Chlorhexidine Gluconate | 12.09% |
| 1% Lauramidopropyl Betaine + 1% P(MA-co-PAM5000) + 0.12% Chlorhexidine Gluconate | 12.60% |

TABLE 3-continued

% Stain prevention

| Sample | % stain prevention |
|---|---|
| 2% Lauramidopropyl Betaine + 2% P(AA-co-PAM5000) + 0.12% Chlorhexidine Gluconate | 37.0% |
| 2% Lauramidopropyl Betaine + 2% P(MA-co-PAM5000) + 0.12% Chlorhexidine Gluconate | 40.0% |

It was observed that adding the polymer/amphoteric blend with the chlorhexidine gluconate reduced staining of teeth significantly when compared with the combination of chlorhexidine and amphoteric surfactant. Furthermore, additional testing revealed that the polymer/amphoteric blend does not interfere with the anti-microbial efficacy of chlorhexidine.

In view of the above-described Examples, it is expected that daily use of the oral care composition in the form of, for example, a toothpaste, tooth gel, dentifrice, tooth powder, prophy paste, mouthwash, rinse, tooth mousse, dental floss, chewing gum, soluble oral care strips or films, or lozenges would provide a powerful, consumer friendly and easy to use arsenal to correct or prevent a wide range of common oral diseases in both humans and other mammals.

The disclosed subject matter has been described with reference to specific details of particular embodiments thereof. It is not intended that such details be regarded as limitations upon the scope of the disclosed subject matter except insofar as and to the extent that they are included in the accompanying claims.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the exemplary embodiments described herein. The exemplary embodiments described herein illustratively disclosed herein suitably may be practiced in the absence of any element that is not specifically disclosed herein and/or any optional element disclosed herein.

What is claimed:
1. An oral care composition comprising:
an orally acceptable carrier;
an amphoteric surfactant having a structure of formula (I):

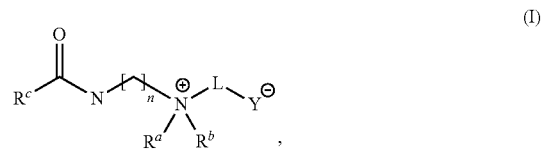

wherein L is a substituted or unsubstituted $(C_2-C_4)$ alkylene,
n is an integer from 1 to 10, $R^a$ and $R^b$ are independently $C_1$-$C_4$ alkyl,
$R^c$ is substituted or unsubstituted $C_1$-$C_{20}$ alkyl, and
Y is an anionic group;
an orally acceptable cationic antibacterial agent; and
a copolymer of i) an allyl phosphate compound; and ii) one or more α, β-ethylenically unsaturated co-monomers, at least one of which is other than an allyl-functional co-monomer,
wherein the allyl phosphate compound has the formula (A):

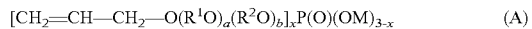

wherein
$R^1$ is a substituted or unsubstituted ($C_2$-$C_4$) alkylene moiety;
$R^2$ is a substituted or unsubstituted ($C_2$-$C_4$) alkylene moiety;
M is identical or different, hydrogen, alkali metal, ammonium, protonated alkyl amine, protonated alkanolamine, or protonated basic amino acid;
X is 1 or 2;
a is from 1 to 20; and
b is from 0 to 20.

2. The oral care composition of claim 1, wherein Y is —C(O)O, or —S(O)$_2$O.

3. The oral care composition of claim 1, wherein n is 2, 3, or 4.

4. The oral care composition of claim 1, wherein $R^a$ and $R^b$ are independently methyl or ethyl.

5. The oral care composition of claim 1, wherein the amphoteric surfactant is selected from the group consisting of cocamidopropyl betaine, lauramidopropyl betaine, cocobetaine, cocamidopropyl hydroxysultaine, and combinations thereof.

6. The oral care composition of claim 1, wherein $R^1$ and $R^2$ are independently substituted with a hydroxyl, alkoxyl, or aryloxyl moiety.

7. The oral care composition of claim 1, wherein the one or more α, β-ethylenically unsaturated co-monomers comprise a moiety selected from the group consisting of maleic anhydride, maleic acid, itaconic anhydride, itaconic acid, and combinations thereof.

8. The oral care composition of claim 1, wherein the orally acceptable cationic antibacterial agent is selected from the group consisting of chlorhexidine gluconate, cetyl pyridium chloride, quaternary ammonium surfactants, cationic amino acids, metal cations, and combinations thereof.

9. The oral care composition of claim 1, wherein the copolymer is polymerized from a mixture comprising one or more α, β-ethylenically unsaturated maleimide phosphate co-monomers, and the one or more α, β-ethylenically unsaturated co-monomers.

10. The oral care composition of claim 9, wherein one of the α, β-ethylenically unsaturated maleimide phosphate co-monomer has the formula (B),

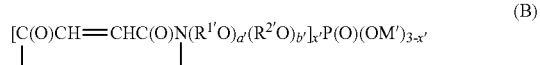

wherein
$R^{1'}$ is a substituted or unsubstituted ($C_2$-$C_4$) alkylene moiety;
$R^{2'}$ is a substituted or unsubstituted ($C_2$-$C_4$) alkylene moiety;

M' is identical or different, hydrogen, alkali metal, ammonium, protonated alkyl amine, protonated alkanolamine, or protonated basic amino acid;
X' is 1 or 2;
a' is from 1 to 20; and
b' is from 0 to 20.

11. The oral care composition of claim 10, wherein $R^{1'}$ and $R^{2'}$ are each independently substituted with a hydroxyl, alkoxyl, or aryloxyl moiety.

12. The oral care composition of claim 1, wherein one of the α, β-ethylenically unsaturated co-monomers has the formula (E):

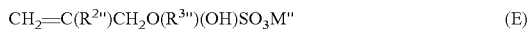

wherein
$R^{2'''}$ is H or an alkyl radical,
$R^{3'''}$ is a linear or branched divalent aliphatic radical which may be hydroxyl substituted,
and
M" is alkali metal, ammonium, protonated alkyl amine, protonated alkanolamine, or protonated basic amino acid.

13. The oral care composition of claim 1, wherein the one or more of the α, β-ethylenically unsaturated co-monomers are selected from the group consisting of allyl ethoxylate, allyl polyethoxylate, methallyl ethoxylate, methallyl polyethoxylate, sodium 1-allyloxy-2-hydroxypropyl sulfonate, sodium 2-acrylamido-2-methylpropane sulfonate, sodium vinyl sulfonate, sodium styrene sulfonate, acrylic acid, methacrylic acid, vinyl acetate, acrylate ester, methacrylate ester, maleate ester, styrene, and combinations thereof.

14. The oral care composition of claim 1, wherein one of the α, β-ethylenically unsaturated co-monomers is a maleimide phosphate compound having a structure of

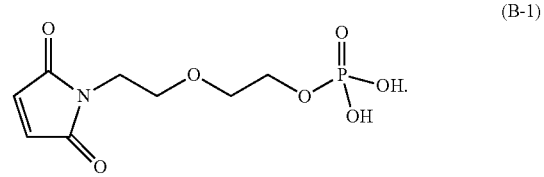 [SMILES: O=C1C=CC(=O)N1CCOCCOP(=O)(O)O]

15. The oral care composition of claim 1, wherein the allyl phosphate compound is of the formula (A-1)

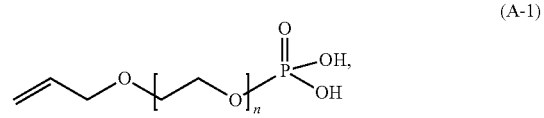

wherein n is 1 to 20.

16. The oral care composition of claim 1, further comprising an abrasive polishing material selected from the group consisting of a silica, an alumina, an orthophosphate, a polyphosphate, a hexametaphosphate, and combinations thereof.

17. The oral care composition of claim 1, further comprising one or more additives selected from the group consisting of a polishing agent, a sudsing agent, a binder, a humectant, a medicinal agent, a sweetening agent, a flavor, a peroxide source, an alkali metal bicarbonate salt, a thickening agent, xylitol, sorbitol, a coloring agent, sodium carbonate, and combinations thereof.

18. The oral care composition of claim 1, wherein the oral care composition is in a form of a toothpaste, tooth gel, dentifrice, tooth powder, prophy paste, mouthwash, rinse, tooth mousse, dental floss, chewing gum, soluble oral care strip or film for direct application or attachment to an oral surface, or lozenge.

19. A method of combating dental caries, erosion, hypersensitivity, and/or staining comprising using the oral care composition of claim 18.

20. A method of treating or preventing dental caries, erosion, hypersensitivity, staining, or a combination thereof comprising using the oral care composition of claim 1.

* * * * *